United States Patent [19]

Berg

[11] Patent Number: 4,966,656

[45] Date of Patent: Oct. 30, 1990

[54] SEPARATION OF STYRENE FROM ETHYL BENZENE OR O-XYLENE BY AZEOTROPIC OR EXTRACTIVE DISTILLATION WITH ESTERS

[75] Inventor: Lloyd Berg, 1314 S. Third Ave., Bozeman, Mont. 59715

[73] Assignee: Lloyd Berg, Bozeman, Mont.

[21] Appl. No.: 533,120

[22] Filed: Jun. 4, 1990

[51] Int. Cl.$^5$ .................. B01D 3/36; B01D 3/40; C07C 7/06

[52] U.S. Cl. .................. 203/060.000; 585/805; 585/806; 585/807; 585/866

[58] Field of Search .................. 203/60; 585/866, 805, 585/806, 807

[56] References Cited

U.S. PATENT DOCUMENTS

| | | | |
|---|---|---|---|
| 2,380,019 | 7/1945 | Bloomer | 585/866 |
| 2,385,235 | 9/1945 | Schneider | 203/64 |
| 2,467,197 | 4/1949 | Engel | 203/60 |
| 2,480,919 | 9/1949 | Greene | 203/60 |
| 3,328,267 | 6/1967 | Müller | 203/60 |
| 3,684,664 | 8/1972 | Abe et al. | 203/60 |
| 3,763,015 | 10/1973 | Morimoto et al. | 203/60 |

FOREIGN PATENT DOCUMENTS 49-16408  4/1974  Japan .................. 585/866

*Primary Examiner*—Wilbur Bascomb

[57] ABSTRACT

Styrene cannot be easily removed from ethyl benzene or o-xylene by distillation because of the closeness of their boiling points. Styrene can be readily separated from ethyl benzene or o-xylene by means of azeotropic or extractive distillation using certain esters. Typical effective agents are ethyl isovalerate, propyl caproate, butyl propionate and hexyl formate.

4 Claims, No Drawings

SEPARATION OF STYRENE FROM ETHYL BENZENE OR O-XYLENE BY AZEOTROPIC OR EXTRACTIVE DISTILLATION WITH ESTERS

FIELD OF THE INVENTION

This invention relates to a method for separating styrene from ethyl benzene or o-xylene using certain esters as the agent in azeotropic or extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid (s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celsius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Ethyl benzene, B.P.=136.2° C., and styrene, B.P.=145.2° C. have a relative volatility of 1.4 and are thus difficult to separate by rectification. Extractive distillation would be an attractive method of effecting the separation of ethyl benzene from styrene if agents can be found that (1) will enhance the relative volatility of ethyl benzene from styrene and (2) are easy to recover from the styrene, that is, form no azeotrope with styrene and boil sufficiently above styrene to make the separation by rectification possible with only a few theoretical plates.

The advantage of using extractive distillation in this separation can be seen from the data presented in Table 1 below.

TABLE 1

Theoretical and Actual Plates Required vs. Relative Volatility for Ethyl Benzene - Styrene Separation

| Relative Volatility | Theoretical Plates Required At Total Reflux, 99% Purity | Actual Plates Required, 75% Eff. |
| --- | --- | --- |
| 1.4 | 27.5 | 37 |
| 1.6 | 19.5 | 26 |
| 1.8 | 15.7 | 21 |
| 2.0 | 13.3 | 18 |
| 2.2 | 11.7 | 16 |
| 2.4 | 10.5 | 14 |

The relative volatility of ethyl benzene to styrene is 1.4 and thus 27.5 theoretical plates are required for separation to 99% purity by conventional rectification at total reflux. Plates possessing an efficiency of 75% are commonly employed and thus 37 actual plates would be required. One of the agents that I have discovered yields a relative volatility as high as 2.4 which would reduce the plate requirement to only 14.

Styrene, b.p.=145.2° C. and o-xylene, b.p.=144.5° C. boil only 0.7 degrees apart and have a relative volatility of only 1.04. Table 2 shows the relationship between relative volatility and plate requirement for rectification. With its relative volatility of only 1.03, the separation of styrene from o-xylene in 99% purity requires 313 plates of 75% efficiency. If a method could be found to increase the relative volatility to 1.8, the plate requirement would be only 21. Extractive distillation would be an attractive method of effecting the separation of styrene from o-xylene if agents can be found that (1) increase the relative volatility of styrene to o-xylene and (2) are easy to recover from o-xylene, that is, form no azeotrope with o-xylene and boil sufficiently above o-xylene to make separation possible with only a few theoretical plates.

TABLE 2

Rectification Column Plates Required for 99% Separation

| Relative Volatility | Theoretical Plates | Actual Plates, 75% Efficiency |
| --- | --- | --- |
| 1.04 | 235 | 313 |
| 1.2 | 50 | 67 |
| 1.4 | 25 | 33 |
| 1.5 | 22 | 29 |
| 1.6 | 19 | 25 |
| 1.7 | 17 | 23 |
| 1.8 | 16 | 21 |

Extractive distillation typically requires the addition of an equal amount to twice as much extractive agent as the styrene - ethyl benzene or styrene - o-xylene mixture on each plate of the rectification column. The extractive agent should be heated to about the same temperature as the plate into which it is introduced. Thus extractive distillation imposes an additional heat requirement on the column as well as somewhat larger plates. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is necessary that the extractive agent be miscible with the styrene, otherwise it will form a two-phase azeotrope with the styrene in the recovery column and some other method of separation will have to be employed.

Azeotropic distillation is an effective means of separating styrene from ethyl benzene or o-xylene if agents can be found that will cause an appreciable increase in the relative volality. Table 2 shows the effect of relative volatility on column plate requirement to obtain 99% purity.

Schneider, U.S. Pat. No. 2,385,235 described the use of ethylene glycol lower alkyl ethers as the azeotrope former to separate styrene from close boiling aromatic hydrocarbons. Bloomer, U.S. Pat. No. 2,398,689 described the use of ethylene glycol methyl ether as the azeotrope former to separate styrene from alkyl benzenes. Engel, U.S. Pat. No. 2,467,197 used ethylene glycol methyl ether and ethylene glycol methyl ether acetate as the azeotrope former to separate styrene from xylenes. Morimoto, U.S. Pat. No. 3,763,015 described the use of dimethylsulfoxide to separate styrene from xylenes by extractive distillation. Abe, U.S. Pat. No. 3,684,665 claims dimethylacetamide, 4-methyl-gamma-butyrolactone, propylene carbonate, gamma-butryolactone and ethylene carbonate as extractive agents for this separation. Haskell, U.S. Pat. No. 4,031,153 lists succinonitrile as being effective. Table 3 lists the experimentally determined relative volatilities for some of these agents.

TABLE 3

Extractive and Azeotropic Distillation Agents Listed in The Literature

| Compound | Rel. Vol. | Compound | Rel. Vol. |
|---|---|---|---|
| Dimethylsulfoxide | 1.38 | Dimethylacetamide | 1.26 |
| Ethylene Carbonate | 1.21 | Propylene Carbonate | 1.21 |
| Dimethylformamide | 1.15 | Sulfolane | 1.19 |
| Ethylene glycol methyl ether | 1.22 | Ethylene glycol methyl ether acetate | 1.26 |

OBJECTIVE OF THE INVENTION

The object of this invention is to provide a process or method of azeotropic or extractive distillation that will enhance the relative volatility of styrene from ethyl benzene or o-xylene in their separation in a rectification column. It is a further object of this invention to identify organic compounds which are stable, can be separated from styrene, ethyl benzene or o-xylene by rectification with relative few plates and can be recycled and reused with little decomposition.

SUMMARY OF THE INVENTION

The objects of the invention are provided by a process for separating styrene from ethyl benzene or o-xylene which entails the use of certain esters as the agent azeotropic or extractive distillation.

DETAILED DESCRIPTION OF THE INVENTION

I have discovered that certain esters will effectively increase the relative volatility of styrene to ethyl benzene or o-xylene and permit the separation of styrene from ethyl benzene or o-xylene by rectification when employed as the agent in azeotropic or extractive distillation.

TABLE 4

Effective Azeotropic Distillation Agents To Separate Styrene From Ethyl Benzene

| Compound | Relative Volatility |
|---|---|
| Ethyl Isovalerate | 2.30 |
| Propyl Butyrate | 1.65 |

TABLE 5

Effective Extractive Distillation Agents To Separate Styrene From Ethyl Benzene

| Compound | Relative Volatility |
|---|---|
| Butyl Butyrate | 2.40 |
| Ethyl Caproate | 1.60 |
| Propyl Caproate | 2.30 |
| Amyl Propionate | 1.95 |
| Methyl Caproate | 1.55 |

TABLE 6

Effective Azeotropic Distillation Agents To Separate Styrene From o-Xylene

| Compound | Relative Volatility |
|---|---|
| Methyl Valerate | 1.80 |
| Butyl Propionate | 1.60 |

TABLE 7

Effective Extractive Distillation Agents To Separate Styrene From o-Xylene

| Compound | Relative Volatility |
|---|---|
| Butyl propionate | 1.45 |
| Ethyl Caproate | 1.80 |
| Hexyl Formate | 1.60 |

The compounds which are effective as azeotrope formers in the separation of styrene from ethyl benzene are ethyl isovalerate and propyl butyrate and are listed with their relative volatilities in Table 4.

The compounds which are effective as extractive distillation agents in the separation of styrene from ethyl benzene are butyl butyrate, ethyl caproate, methyl caproate, propyl caproate and amyl propionate and are listed with their relative volatilities in Table 5.

The compounds which are effective as azeotrope formers in the separation of styrene from o-xylene are methyl valerate and butyl propionate and are listed with their relative volatilities in Table 6.

The compounds which are effective as extractive distillation agents in the separation of styrene from o-xylene are butyl propionate, ethyl caproated and hexyl formate and are listed with their relative volatilities in Table 7.

The data listed in Tables 4–7 was obtained in a vapor-liquid equilibrium still.

A number of esters of similar structure and molecular weight were investigated and found to be ineffective. They are isobutyl butyrate, isobutyl isobutyrate, hexyl acetate, methyl amyl acetate, phenyl acetate, ethyl phenyl acetate, methyl acetoacetate, isobornyl acetate, diethyl maleate, ethyl benzoate, methyl heptanoate, ethyl heptanoate, ethyl valerate, dimethyl malonate and 2-ethyl hexyl acetate.

THE USEFULNESS OF THE INVENTION the usefulness or utility of this invention can be demonstrated by referring to the data presented in Tables 1–7. All of the successful agents show that styrene can be separated from ethyl benzene or o-xylene by means of azeotropic or extractive distillation in a rectification column and that the ease of separation as measured by relative volatility is considerable. Without these agents, little improvement will occur in a rectification column. Table 1 shows that ethyl benzene and styrene have a relative volatility of 1.40 and Table 2 shows that o-xylene and styrene have a relative volatility of only 1.04. The data also show that the most attractive agents will operate at a boil-up rate low enough to make this a useful and efficient method of recovering styrene from ethyl benzene or o-xylene from any mixture of these compounds. The stability of the agents used and the boiling point difference is such that complete recovery and recycle is obtainable by a simple distillation and the amount for make-up is small.

WORKING EXAMPLES

Example 1—Twenty grams of ethyl benzene, ten grams of styrene and thirty grams of ethyl isovalerate were charged to a vapor-liquid equilibrium still and refluxed for 3/4 hours at 60 mm. Hg. Analysis indicated a vapor azeotrope composition of 87.2% ethyl benzene, 12.8% styrene; a liquid composition of 74.4% ethyl benzene, 25.6% styrene which is a relative volatility of 2.30.

Example 2: Twenty grams of ethyl benzene, ten grams of styrene and twenty grams of propyl caproate were charged to the vapor-liquid equilibrium still and refluxed for a half hour at 60 mm. Hg. Analysis indicated a vapor composition of 69.3% ethyl benzene, 30.7% styrene; a liquid composition of 49.2% ethyl benzene, 50.8% styrene which is a relative volatility of 2.3.

Example 3: Twenty grams of o-xylene, ten grams of styrene and 30 grams of methyl valerate were charged to the vapor-liquid equilibrium still and refluxed for one hour at 60 mm. Hg. Analysis indicated a vapor azeotrope composition of 79.2% o-xylene, 20.8% styrene; a liquid composition of 67.7% o-xylene, 32.3% styrene which is a relative volatility of 1.82.

Example 4: Twenty grams of o-xylene, ten grams of styrene and 20 grams of hexyl formate were charged to the vapor-liquid equilibrium still and refluxed for a half hour at 60 mm. Hg. Analysis indicated a vapor composition of 76.5% o-xylene, 23.5% styrene; a liquid composition of 66.7% o-xylene, 33.3% styrene which is a relative volatility of 1.60.

I claim:

1. A method for recovering styrene from mixtures of styrene and ethyl benzene which comprises distilling a mixture of styrene and ethyl benzene in a rectification column in the presence of an azeotrope forming agent, recovering ethyl benzene and the azeotrope forming agent as overhead product and the styrene from the stillpot, wherein said azeotrope forming agent comprises one material selected from the group consisting of ethyl isovalerate and propyl butyrate.

2. A method for recovering styrene from mixtures of styrene and ethyl benzene which comprises distilling a mixture of styrene and ethyl benzene in a rectification column in the presence of about one part of an extractive agent per part of styrene - ethyl benzene mixture, recovering the ethyl benzene as overhead product and the styrene and the extractive agent from the stillpot, wherein said extractive agent comprises one material selected from the group consisting of amyl propionate, butyl butyrate, ethyl caproate, methyl caproate and propyl caproate.

3. A method for recovering styrene from mixtures of styrene and o-xylene which comprises distilling a mixture of styrene and o-xylene in a rectification column in the presence of a azeotrope forming agent, recovering the o-xylene and the azeotrope forming agent as overhead product and the styrene from the stillpot, wherein said azeotrope forming agent comprises one material selected from the group consisting of methyl valerate and butyl propionate.

4. A method for recovering styrene from mixtures of styrene and o-xylene which comprises distilling a mixture of styrene and o-xylene in a rectification column in the presence of about one part of an extractive agent per part of styrene - o-xylene mixture, recovering the o-xylene as overhead product and the styrene and the extractive agent from the stillpot, wherein said extractive agent comprises one material selected from the group consisting of butyl propionate, ethyl caproate and hexyl formate.

* * * * *